United States Patent

Proudfoot et al.

Patent Number: 5,908,841
Date of Patent: Jun. 1, 1999

[54] 5,11-DIHYDRO-6H-DIPYRIDO[3,2-B:2',3'-E] AZEPINE-6-ONES AND THEIR USE IN THE PREVENTION OF TREATMENT OF HIV INFECTION

[75] Inventors: John R. Proudfoot, Newtown; Karl D. Hargrave, Brookfield, both of Conn.

[73] Assignee: Boehringer Ingelheim Pharmaceuticals, Inc., Ridgefield, Conn.

[21] Appl. No.: 09/132,527

[22] Filed: Aug. 11, 1998

Related U.S. Application Data

[60] Provisional application No. 60/055,189, Aug. 11, 1997.
[51] Int. Cl.$^6$ ........................ A61K 31/55; C07D 487/00; C07D 491/00; C07D 498/00
[52] U.S. Cl. ............................ 514/215; 540/521
[58] Field of Search ............................. 514/215; 540/521

[56] References Cited

U.S. PATENT DOCUMENTS 5,366,972  11/1994  Hargrave et al. ........................ 514/220

OTHER PUBLICATIONS

Kelly et al. (J. Med. Chem. (1995), 38(24), 4839–470).
Hargrave et al. (J. Med. Chem. (1991), 34, 2231–2241).
Dalpiaz et al. (J. Med. Chem. (1995), 38, 4730–4738).

*Primary Examiner*—Richard L. Raymond
*Assistant Examiner*—Bruck Kifle
*Attorney, Agent, or Firm*—Robert P. Raymond; Alan R. Stempel; Mary-Ellev Devlin

[57] ABSTRACT

There are disclosed compounds of the formula 1

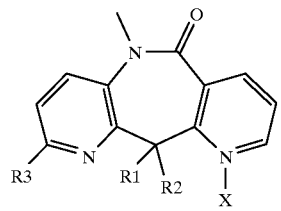

wherein X is an oxygen atom or nothing and R1, R2 and R3 are as defined in the specification, useful in the prevention or treatment of HIV infection.

6 Claims, No Drawings

5,11-DIHYDRO-6H-DIPYRIDO[3,2-B:2',3'-E] AZEPINE-6-ONES AND THEIR USE IN THE PREVENTION OF TREATMENT OF HIV INFECTION

CROSS-REFERENCE TO RELATED APPLICATIONS

The benefit of prior provisional application Ser. No. 60/055,189, filed on Aug. 11, 1997, is hereby claimed.

FIELD OF THE INVENTION

The invention relates to novel 5,11-dihydro-6H-dipyrido [3,2-b:2',3'-e]azepine-6-ones and pharmaceutically acceptable salts thereof, methods for preparing these compounds, the use of these compounds either alone or in combination with other anti-virals, immunomodulators, antibiotics, anti-infectives, or vaccines in the prevention or treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandeering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins. The conversion of the RNA to DNA is accomplished through the use of the enzyme reverse transcriptase (RT), which is included within the infecting virion along with the RNA. Reverse transcriptase has three known enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Acting as a ribonuclease, RT frees the DNA just produced from the original viral RNA and destroys the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds which inhibit the enzymatic functions of HIV-1 reverse transcriptase will inhibit replication of HIV-1 in infected cells.

A number of compounds that inhibit the enzymatic functions of HIV-1 reverse transcriptase are known. One class of known HIV-1 RT inhibitors is the nucleoside analogs. This class includes 3'-azido-3'-deoxythymidine (AZT), 2',3'-dideoxyinosine (ddI), and 2',3'-dideoxy-cytidine (ddC). Another class is the non-nucleoside analogs. This class includes, inter alia, nevirapine, which is 11-cyclopropyl-5,11-dihydro-4-methyl-6H-dipyrido[3,2-b:2',3'-e][1,4]-diazepin-6-one. Nevirapine and other paricularly relevant compounds of the non-nucleoside class are described in U.S. Pat. No. 5,366,972; by Hargrave et al.,"Novel Non-Nucleoside Inhibitors of HIV-1 Reverse Transcriptase. 1. Tricyclic Pyridobenzo-and Dipyridodiazepinones", *J. Med. Chem.*, 34, 2231 (1991); and by Proudfoot et al., "Novel Non-Nucleoside Inhibitors of HIV-1 Reverse Transcriptase. 4.2-Substituted Dipyridodiazepinones are Potent Inhibitors of both Wild Type and Cysteine-181 HIV-1 Reverse Transcriptase Enzymes". *J. Med. Chem.*, 38, 4830–4838 (1995).

OBJECT OF THE INVENTION

As with any anti-viral therapy, use of RT inhibitors in the treatment of HIV-1 infection tends to produce virus which is less sensitive to the given drug. Resistance (reduced sensitivity) to these drugs is the result of mutations which occur in the reverse transcriptase segment of the pol gene.

The object of the present invention is to provide improved, non-nucleoside inhibitors of HIV-1 RT which are more potent against mutant strains of HIV-1 than the known compounds of this class.

The compounds of the present invention satisfy this object in that they are highly potent against not only the wild-type (non-mutated) virus RT enzyme, but are also effective against the Y181C mutant [in which the tyrosine (Y) at codon 181 has been mutated to a cysteine (C) residue] which has been the most commonly observed mutant in clinical studies following therapy with many non-nucleoside reverse transcriptase inhibitors.

SUMMARY OF THE INVENTION

A first aspect of the invention comprises novel 5,11-dihydro-6H-dipyrido[3,2-b:2',3'-e]azepine-6-ones. These possess inhibitory activity against both wild-type and mutant HIV-1 RT. A second aspect of the invention comprises methods for making these novel compounds. A third aspect of the invention is a method for inhibiting replication of HIV-1 in a human host infected by HIV-1. A fourth aspect of the invention is a method for preventing or treating HIV-1 infection which comprises administering, to a human being exposed to or infected by HIV-1, a prophylactically or therapeutically effective amount of one of the above-mentioned novel compounds, either alone or in combination with other anti-viral agents, immunomodulators, antibiotics, anti-infectives, or vaccines. A final aspect of the invention comprises pharmaceutical compositions suitable for the prevention or treatment of HIV-1 infection comprising the above-mentioned compounds.

DESCRIPTION OF THE INVENTION

In one of its composition of matter aspects, the invention comprises 5,11-dihydro-6H-dipyrido[3,2-b:2',3'-e]azepine-6-ones of formula 1

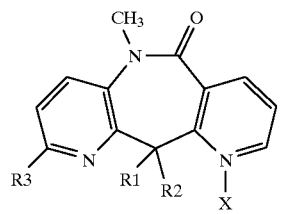

1 wherein;

X is an oxygen atom or nothing;

$R^1$ is hydrogen, alkyl of 1 to 4 carbon atoms, fluoroalkyl of 1 to 4 carbon atoms and 1 to 3 fluorine atoms, cycloalkyl of 3 to 6 carbon atoms, alkylthio of 1 to 2 carbon atoms, alkyloxy of 1 to 2 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 4 carbon atoms, alkyloxyalkyl or alkylthioalkyl of 2 to 3 carbon atoms, alkanoyl or alkyl(thiocarbonyl) of 2 to 5 carbon atoms, or cyanoalkyl of 2 to 3 carbon atoms;

$R^2$ is hydrogen, methyl or ethyl;

$R^3$ is a hydrogen atom, alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxy or alkylthio of 2 to 6 carbon atoms, alkyloxyalkyl or alkylthioalkyl of 2 to 6 carbon atoms, pyrrolidinyl, pyrrolinyl, piperidinyl, mono-or di-alkylamino wherein each alkyl moiety contains 1 to 3 carbon atoms, halogen, cyano, nitro, or carboxyl, aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by hydroxyl, amino, halogen, alkyl or alkyloxy of 1 to 3 carbon atoms.

A subgeneric aspect of the invention comprises compounds of formula 1, wherein:

X is nothing;

$R^1$ is hydrogen, alkyl of 1 to 3 carbon atoms, cycloalkyl of 3 to 4 carbon atoms, alkylthio of 1 to 2 carbon atoms;

$R^2$ is hydrogen, methyl or ethyl;

$R^3$ is a hydrogen atom, methyl, trihalomethyl, alkyloxy or alkylthio of 1 to 2 carbon atoms, pyrrolidinyl, pyrrolinyl, piperidinyl, di-alkylamino wherein each alkyl moiety contains 1 to 2 carbon atoms, halogen, cyano, aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by hydroxyl, amino, halogen, alkyl or alkyloxy of 1 to 3 carbon atoms.

A particular subgeneric aspect of the invention comprises compounds of formula 1, wherein:

X is nothing;

$R^1$ is ethyl, cyclopropyl, or methylthio;

$R^2$ is hydrogen;

$R^3$ is hydrogen, chloro, methoxy or 4-pyrazolyl.

Preferred compounds of formula 1 are:

5-methyl-11-ethyl-2-(4-pyrazolyl)-5,11-dihydro-6H-dipyrido[3,2-b:2',3'-e]azepine;

5-methyl-11-ethyl-2-methoxy-5,11-dihydro-6H-dipyrido[3,2b:2',3'-e]azepine.

Synthesis Of Compounds Of Formula 1 And Their Salts

The compounds of Formula 1 and their salts can be prepared by known methods, or obvious modifications thereof, in accordance with the general synthetic scheme shown below.

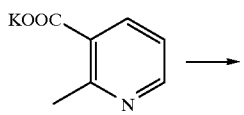

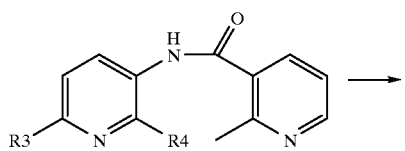

R3 = H, Cl, OMe
R4 = Cl, Br

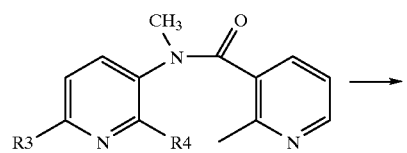

R3 = H, Cl, OMe
R4 = Cl, Br

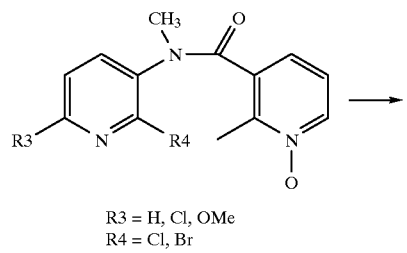

R3 = H, Cl, OMe
R4 = Cl, Br

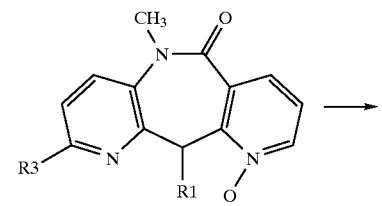

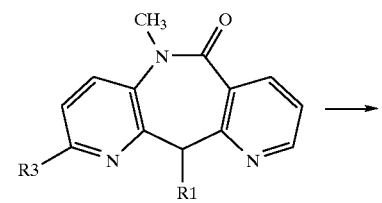

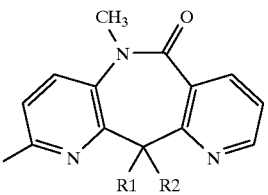

Method A
Compounds of formula 1

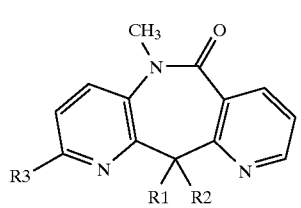

1 wherein $R^1$ through $R^3$ are as defined above, and $R^1$ and $R^2$ are not both hydrogen maybe obtained from a compound of formula 1 wherein one of $R^1$ or $R^2$ is hydrogen by conversion to the corresponding, wherein $M^+$ represents an alkali metal such as lithium, sodium or potassium, in an inert solvent such as TETRAHYDROFURAN, DMSO or the like, and subsequently reacting it with a compound of formula $R^2$—X wherein $R^2$ is as previously defined, and X is the radical of a reactive ester, a halogen atom, methanesulfonyloxy, trifluoromethanesulfonyloxy or an aromatic sulfonyloxy group.

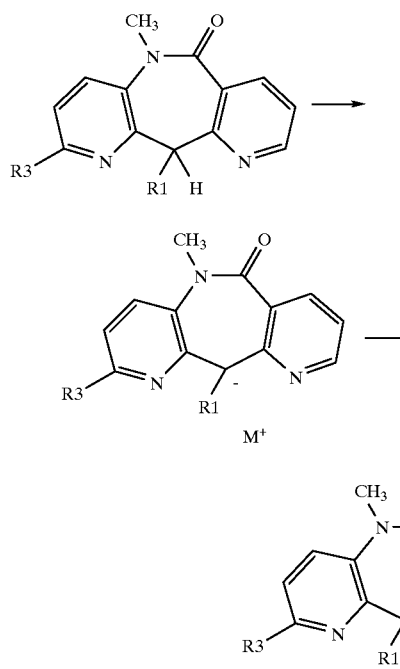

Compounds of formula 1

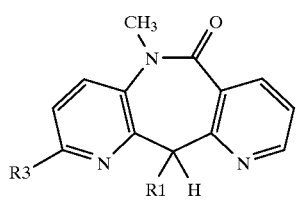

wherein $R^1$ through $R^3$ are as defined above, may be obtained from a compound of formula 2 by deoxygenation with reagents such as phosphorus trichloride in an inert solvent such as chloroform, or Lawessons reagent in an inert solvent such as toluene at some temperature between room temperature and the boiling point of the solvent.

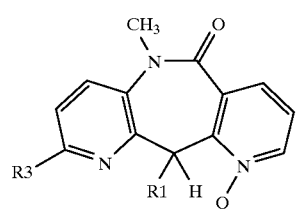

Compounds of formula 2

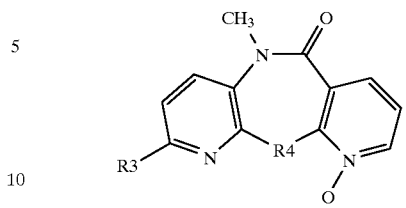

wherein $R^1$ through $R^3$ are as defined above, may be obtained from a compound of formula 3 wherein $R^1$ through $R^3$ are as defined above, and $R^4$ is a chloro or bromo substituent, by conversion to the corresponding metal salt 4, wherein $M^+$ represents an alkali metal such as lithium, sodium or potassium, in an inert solvent such as TETRAHYDROFURAN, DMSO or the like, and subsequently reacting the cyclized intermediate 5 with a compound of formula $R^1$—X wherein $R^1$ is as previously defined and X is the radical of a reactive ester, a halogen atom, methanesulfonyloxy, trifluoromethanesulfonyloxy or an aromatic sulfonyloxy group, or by reacting 5 with a compound of formula $R^1$—S—S—$R^1$ wherein $R^1$ is as previously defined.

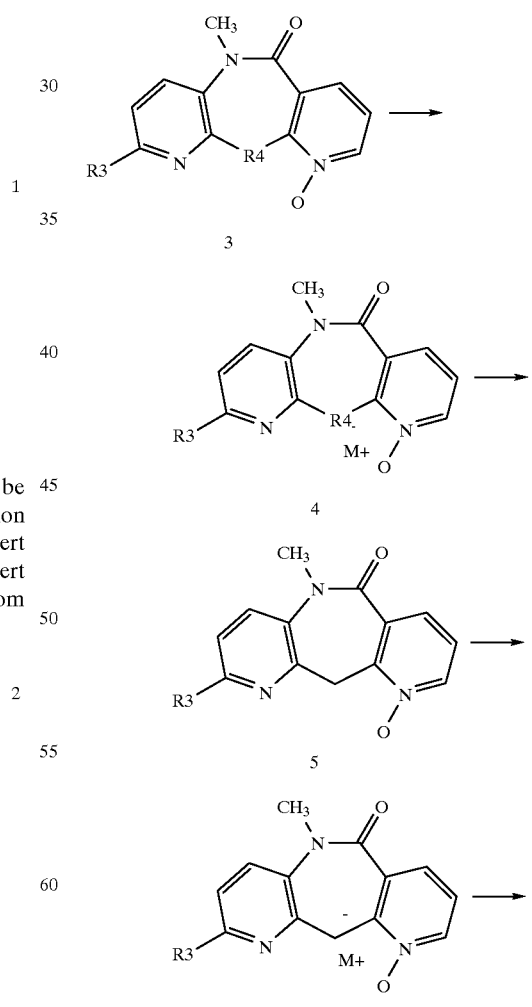

-continued

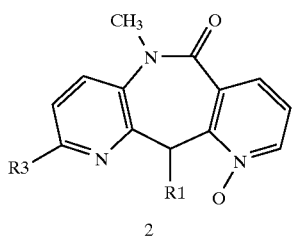

2

Compounds of formula 3

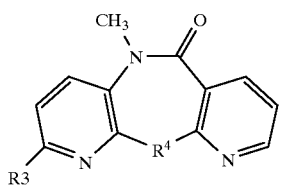

7 wherein $R^3$ and $R^4$ are as described above may be obtained from a compound of formula 7 by reaction with hydrogen peroxide in acetic acid at the boiling point of the solvent.

2-Chloronicotinic acid amides of general formula 7 can be obtained by condensation of 2-methylnicotinic acid chloride with an appropriately substituted 3-amino-2-halopyridine, under well known reaction conditions.

All the other starting materials needed to prepare compounds of the formula 1 are known from the literature, or may be purchased, or may be obtained by procedures known from the literature.

Formation Of Salts And Other Derivatives

Compounds of formula 1 may, if desired, be converted into their non-toxic, pharmaceutically acceptable addition salts by conventional methods; for example, by dissolving a compound of formula 1 in a suitable solvent and treating the solution with one or more molar equivalents of the desired acid or base, as appropriate. The invention also comprises such salts.

Examples of inorganic and organic acids which may form nontoxic, pharmaceutically acceptable acid addition salts with a compound of the formula 1 are the following: hydrochloric acid, hydrobromic acid, sulfuric acid, phosphoric acid, nitric acid, methanesulfonic acid, tartaric acid, fumaric acid, acetic acid, and the like. Examples of inorganic and organic bases which may form nontoxic, pharmaceutically acceptable basic addition salts with a compound of the formula 1 are the following: sodium hydroxide, potassium hydroxide, magnesium hydroxide, ammonia, tromethamine, and the like. Compounds of formula 1 may form addition salts with one molar equivalent of the acid or base, as appropriate.

It will be obvious to those skilled in the art that in some instances the reactions described in Methods A to H cannot be effected in the presence of reactive intermediates incompatible with the reaction conditions. In such cases, the reactive substituent must first be derivatized via known per se methods to contain a suitable protective group, which can then be subsequently removed.

Biological Properties

The above described compounds of formula 1 possess inhibitory activity against HIV-1 reverse transcriptase. By inhibiting HIV-1 reverse transcriptase, they ultimately inhibit or suppress the ability of the virus to integrate its genome into the genome of potential host cells, which, in turn, inhibits or suppresses viral replication. When administered in suitable dosage forms, alone or in combination with other anti-virals, immunomodulators, antibiotics, anti-infectives, or vaccines, they are, thus, useful in the prevention or treatment of HIV-1 infection. Another aspect of the invention, therefore, is a method for preventing or treating HIV-1 infection which comprises administering to a human being, exposed to or infected by HIV-1, a prophylactically or therapeutically effective amount of a novel compound of formula 1, as described above.

As the term is used herein, infection by HIV-1 constitutes the replication of HIV-1 in a human host.

As the term is used herein, the treatment of HIV-1 infection comprises the partial or total inhibition or suppression of replication of HIV-1 in a human host in whom replication of the virus has already begun to take place.

As the term is used herein, the prevention of HIV-1 infection comprises the complete prevention of the establishment of viral replication in a human host who has been exposed to HIV-1 but in whom replication of the virus has not yet begun to take place.

The compounds of the present invention are effective agents for the treatment of HIV-1 infection by virtue of their ability to partially or totally inhibit or suppress replication of HIV-1 in an infected human host.

When used to treat HIV-1 infection, the compounds of the present invention can be administered either before or after the onset of clinical manifestations of HIV-1 infection, such as ARC or AIDS.

The compounds of the present invention are effective for the prevention of HIV-1 infection in humans, by virtue of their ability to prevent the establishment of viral replication in a human host who has been exposed to HIV-1 but in whom replication of the virus has not yet begun to take place.

The compounds of formula 1 may be administered in single or divided doses by the oral, parenteral or topical routes. A suitable oral dosage for a compound of formula 1 would be in the range of about 100 mg to 3 g per day. A preferred oral dosage for a compound of formula 1 would be the maximum tolerated dose, which would typically be in the range of between about 200 mg and 2 g per day. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula 1 can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

The compounds of the invention may be administered either alone or in combination with other anti-virals, immunomodulators, antibiotics, anti-infectives, or vaccines. For example the compounds of the invention may be administered in combination with one or more of the known nucleoside analog HIV reverse transcriptase inhibitors, such as AZT, ddI and ddC, other non-nucleoside HIV reverse transcriptase inhibitors, or HIV protease inhibitors.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. It is known (data not shown) that they also inhibit the DNA-dependent DNA polymerase activity of HIV-1 RT.

Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table I, below.
REVERSE TRANSCRIPTASE (RT) ASSAYS
Assay Theory:
Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate. The assay described below utilizes the wild type (WT) enzyme, which is the predominant form of the enzyme observed in patients infected with HIV-1. Utilization of mutant RT enzymes (Y181C and Y181L, prepared by site-directed mutagenesis in which the tyrosine residue at codon 181 has been replaced by a cysteine or a leucine residue, respectively) and analogous assay conditions allows compounds to be evaluated for their effectiveness at inhibiting these mutant enzymes.
Materials:

a) Preparation of the wild type enzyme Reverse transcriptase enzyme from the LAV strain of Human Immunodeficiency Virus (HIV-1) (1) was isolated from the bacterial strain JM109 (3) expressing the DNA clone pBRTprtl+ (2) which is under the control of the lac promotor in the expression vector pIBI21 (4). An overnight culture grown in 2XYT medium (37° C., 225 rpm) (5) supplemented with 100 μg/mL ampicillin for positive selection is inoculated at a 1:40 dilution into M9 medium supplemented with 10 μg/mL thiamine, 0.5% casamino acids, and 50 μg/mL ampicillin (5). The culture is incubated (37° C., 225 rpm) until it reaches an OD540 of 0.3–0.4. At that time the repressor inhibitor IPTG (isopropyl β-D-thiogalactopyranoside) is added to 0.5 mM, and the mixture is incubated for 2 additional hours. Bacteria are pelleted, resuspended in a 50 mM Tris, 0.6 mM EDTA, 0.375M NaCl buffer and digested by the addition of lysozyme (1 mg/mL) for 30 minutes on ice. The cells are lysed by the addition of 0.2% NP-40 and brought to 1M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

b) Composition of 2× concentrated stock reaction mixture

| Stock Reagent | 2X Mix Concentration |
| --- | --- |
| 1M Tris pH 7.4 | 100 mM |
| 1M dithiothrietol | 40 mM |
| 1M NaCl | 120 mM |
| 1% Nonidet P-40 | 0.1% |
| 1M MgCl | 4 mM |
| [poly r(C)/oligo d(G)] (5:1) | 2 μg/mL |
| $^3$H-DgTP (81 μM) | 0.6 μM |

Assay Procedure:

The 2× concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 μL/well; 3 wells/compound). The HIV-1 RT enzyme is thawed, diluted in 50 mM Tris pH 7.4 so that fifteen μL of diluted enzyme contain 0.001 Unit (one unit is that amount of enzyme to transform 1 micromole of substrate per minute at 25° C.), and fifteen μL are dispensed per well. Twenty μL of 0.12–0.5M EDTA are added to the first three wells of the microtiter plate. EDTA chelates the Mg$^{++}$ present and prevents reverse transcription. This group serves as background polymerization which is subtracted from all other groups. Twenty-five µl of the 2× reaction mixture are added to all wells and the assay is allowed to incubate at room temperature for 60 minutes. The assay is terminated by precipitating the DNA in each well with 50 µL of 10% trichloracetic acid (TCA) (10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mL of scintillation cocktail and is counted in a Beckman beta counter. The calculation for percent inhibition is as follows:

$$\% \text{ inhibition} = \frac{CPM \text{ Mean Test Value} - CPM \text{ Mean Control Value}}{CPM \text{ Mean Control Value}} \times 100$$

References:

1. Benn, S., et al., *Science* 230:949, 1985
2. Farmerie, W. G. et. al., *Science* 236:305, 1987
3. Yanisch-Perron, C., Viera, J., and Messing, J., *Gene* 33:103, 1985
4. International Biotechnologies, Inc., New Haven, Conn. 06535
5. Maniatis, T, Fritsch, E. F., and J. Sambrook, eds. *Molecular Cloning: A Laboratory Manual*, Cold Spring Harbor Laboratory, 1982
6. Spira, T., et. al. *J. Clinical Microbiology*, 25:97, 1987.

TABLE I

| Compound of Example No | Reverse Transciptase Assay % inhibition (1 µM) | |
|---|---|---|
| | WT | Y181C |
| 1 | 68% | 34% |
| 2 | 62% | 14% |
| 3 | 64% | 0% |
| 4 | 68% | 9% |
| 5 | 62% | 18% |
| 6 | 62% | 15% |
| 7 | 75% | 21% |
| 8 | 84% | 24% |
| 9 | 66% | 26% |
| 10 | 91% | 46% |
| 11 | 80% | 33% |
| 12 | 41% | 30% |
| 13 | 80% | 56% |

EXAMPLES

The following examples further illustrate the present invention and will enable others skilled in the art to understand it more completely. It should be understood, however, that the invention is not limited to the particular examples given below.

Example 1

5,11-Dihydro-11-ethyl-5-methyl-10-oxo-6H-dipyrido[3,2-b:2',3'-e]azepin-6-one

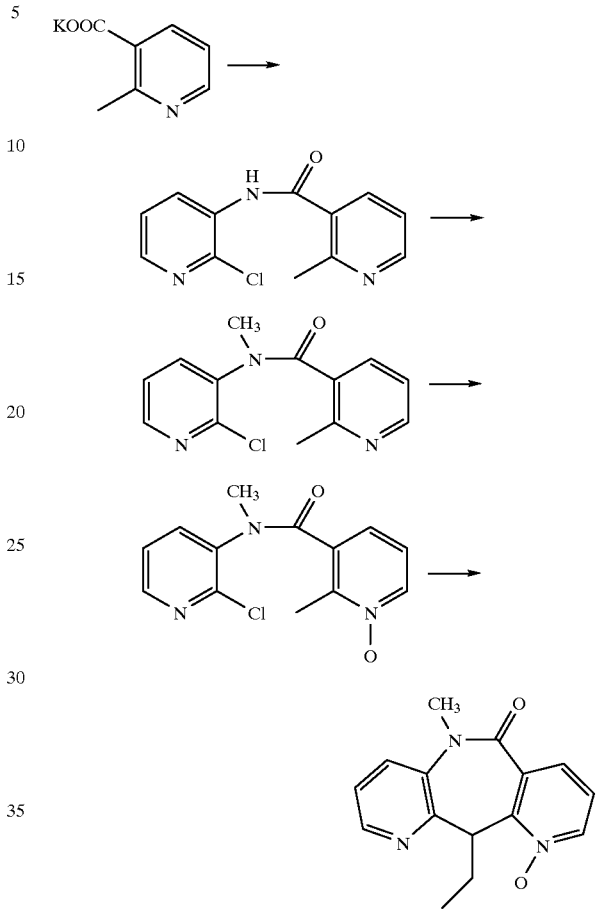

N-(2-chloro-3-pyridinyl)-2-methylnicotinamide.

To a suspension of potassium 2-methylnicotinate (1.82 g) in chloroform (30 mL) was added thionyl chloride (2.0 mL). The mixture was stirred overnight at room temperature under a drying tube. The solvent was evaporated and the residue was taken up in ethyl acetate. 3-Amino-2-chloropyridine (1.28 g) was added followed by diisopropylethylamine (4.0 mL). The reaction mixture was stirred at room temperature under a drying tube for 3 hours. The mixture was diluted with chloroform, washed with water, dried ($Na_2SO_4$), filtered, and evaporated Chromatography of the residue over silica gel (ethyl acetate/hexane) gave N-(2-chloro-3-pyridinyl)-2-methylnicotinamide (1.94 g).

N-(2-chloro-3-pyridinyl)-N-methyl-2-methylnicotinamide.

To a stirred solution of N-(2-chloro-3-pyridinyl)-2-methylnicotinamide (1.48 g) in DMSO (20 mL) was added NaH (60% in oil, 0.26 g). After 20 minutes, methyl iodide (0.45 mL) was added, and stirring was continued for 30 minutes. The mixture was diluted with ethyl acetate, washed with water, dried ($Na_2SO_4$), filtered, and evaporated. Chromatography of the residue over silica gel (ethyl acetate/hexane) gave N-(2-chloro-3-pyridinyl)-N-methyl-2-methylnicotinamide (1.51 g).

N-(2-chloro-3-pyridinyl)-N-methyl-2-methylnicotinamide N-oxide.

A mixture of N-(2-chloro-3-pyridinyl)-N-methyl-2-methylnicotinamide (1.86 g) and $H_2O_2$ (30%, 5 mL) in acetic acid (10 mL) was heated at 110° C. for 75 minutes. The solvents were evaporated under reduced pressure. Chromatography of the residue over basic alumina (chloroform/ethanol) gave N-(2-chloro-3-pyridinyl)-N-methyl-2-methylnicotinamide N-oxide as an oil which crystallized on trituration with isopropyl ether/ethyl acetate, (1.42 g).

5,11-dihydro-11-ethyl-5-methyl-10-oxodipyrid[3,2-b:2',3'-e]azepine-6-one.

To a stirred solution of N-(2-chloro-3-pyridinyl)-N-methyl-2-methylnicotinamide N-oxide (1.11 g) in tetrahydrofuran (15 mL) under nitrogen, cooled on ice, was added dropwise potassium tert-butoxide (1M in tetrahydrofuran, 8.5 mL) over 5 minutes. The mixture was allowed to warm to room temperature, stirred for 30 minutes, and ethyl iodide (0.35 mL) was added. After 90 minutes, the mixture was diluted with chloroform, and washed with water. The aqueous phase was back extracted with chloroform and the combined organic phase was dried ($Na_2SO_4$), filtered, and evaporated. Chromatography of the residue over basic alumina (methylene chloride/ethanol) gave 5,11-dihydro-11-ethyl-5-methyl-10-oxodipyrid[3,2-b:2',3'-e]azepine-6-one (0.75 g).

Example 2

5,11-Dihydro-11-ethyl-5-methyldipyrido[3,2-b:2',3'-e]azepine-6-one

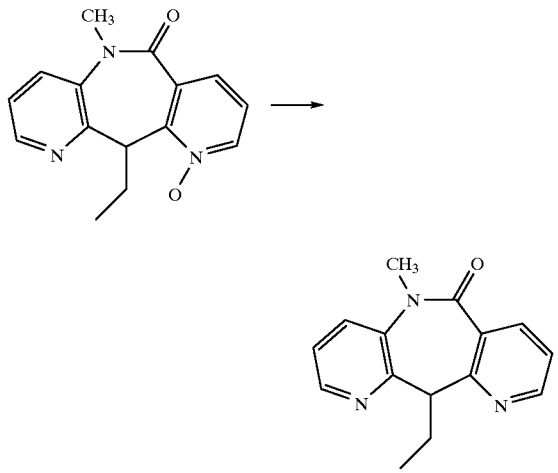

To a solution of 5,11-dihydro-11-ethyl-5-methyl-10-oxodipyrido[3,2-b:2',3'-e]azepine-6-one (0.328 g) in chloroform (10 mL) cooled on ice was added phosphorus trichloride (1.0 mL). The mixture was heated under reflux for 10 minutes, cooled, and added to aqueous NaOH (15% solution, 10 mL). Chloroform (50 mL) was added, and the organic phase was separated, dried ($Na_2SO_4$), filtered, and evaporated. Chromatography of the residue over silica gel (ethyl acetate/ethanol) gave 5,11-dihydro-11-ethyl-5-methyldipyrido[3,2-b:2',3'-e]azepine-6-one (0.209 g).

Example 3

5,11-Dihydro-11-propyl-5-methyldipyrido[3,2-b:2',3'-e]azepine-6-one

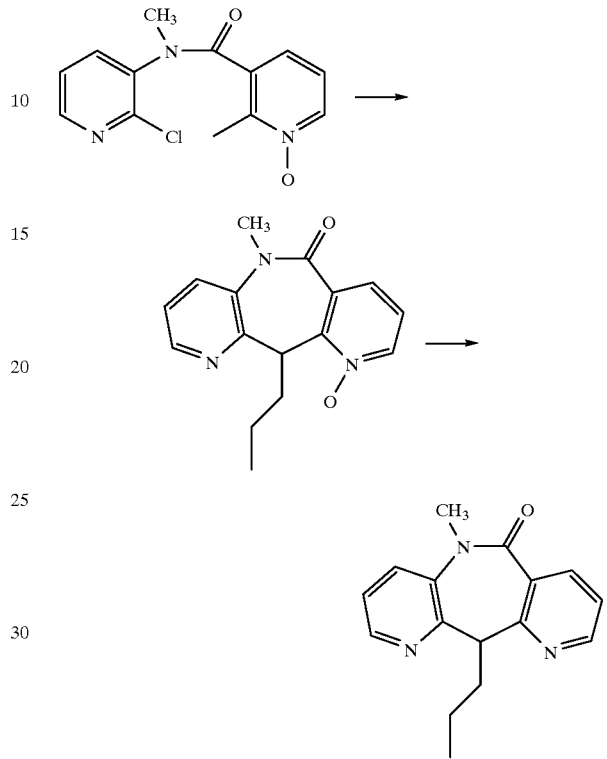

5,11-dihydro-11-propyl-5-methyl-10-oxodipyrid[3,2-b:2',3'-e]azepine-6-one

To a stirred solution of N-(2-chloro-3-pyridinyl)-N-methyl-2-methylnicotinamide N-oxide (0.553 g) in tetrahydrofuran (10 mL) under nitrogen, cooled on ice, was added dropwise sodium bis(trimethylsilyl)amide (1M in tetrahydrofuran, 5 mL). After 5 minutes the mixture was allowed to warm to room temperature, and propyl iodide (0.30 mL) was added. After 3 hours, water was added, the mixture was diluted with chloroform, and the organic phase was separated, washed, dried ($Na_2SO_4$), filtered, and evaporated. Chromatography of the residue over basic alumina (chloroform/ethanol)) gave 5,11-dihydro-11-propyl-5-methyl-10-oxodipyrid[3,2-b:2',3'-e]azepine-6-one (0.255 g) which was used directly in the next step.

5,11-dihydro-11-propyl-5-methyl-dipyrid[3,2-b:2',3'-e]azepine-6-one

To a solution of 5,11-dihydro-11-propyl-5-methyl-10-oxodipyrido[3,2-b:2',3'-e]azepine-6-one (0.255 g) in chloroform (10 mL) cooled on ice was added phosphorus trichloride (0.3 mL). The mixture was heated under reflux for 10 minutes, cooled, and quenched with aqueous NaOH (5% solution). Chloroform (50 mL) was added, and the organic phase was separated, dried ($Na_2SO_4$), filtered, and evaporated. Chromatography of the residue over silica gel (ethyl acetate/hexane) gave 5,11-dihydro-11-propyl-5-methyldipyrido[3,2-b:2',3'-e]azepine-6-one (0.10 g).

Example 4

5,11-Dihydro-11-ethyl-11-methyl-5-methyldipyrido[3,2-b:2',3'-e]azepine-6-one

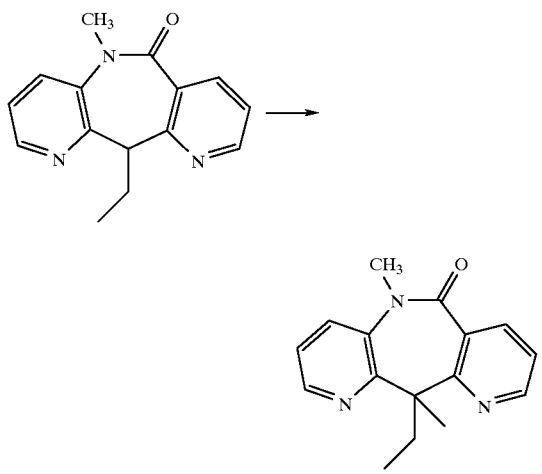

To a solution of 5,11-dihydro-11-ethyl-5-methyldipyrido[3,2-b:2',3'-e]azepine-6-one (0.10 g) in DMSO (1 mL) stirred under nitrogen was added potassium tert-butoxide (1M in tetrahydrofuran, 0.5 mL). After 3 minutes, methyl iodide (0.1 mL) was added, and the mixture was stirred for 10 minutes. Ethyl acetate was added, and the mixture was washed with water, dried, filtered, and evaporated. The residue was fractionated by preparative layer chromatography (developer chloroform/ethanol) to give 5,11-dihydro-11-ethyl-11-methyl-5-methyldipyrido[3,2-b:2',3'-e]azepine-6-one (0.006 g).

Example 5

5,11-Dihydro-11-diethyl-5-methyldipyrido[3,2-b:2',3'-e]azepine-6-one

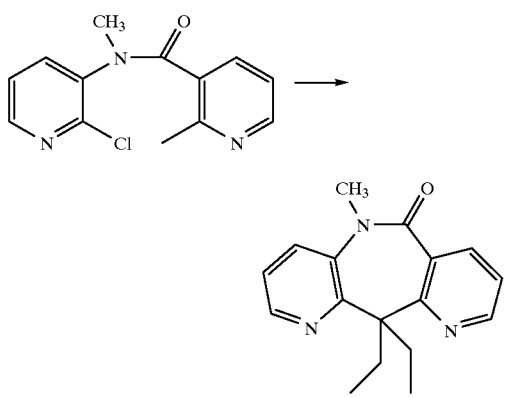

To a stirred solution of N-(2-chloro-3-pyridinyl)-N-methyl-2-methylnicotinamide (0.523 g) in tetrahydrofuran (10 mL) under nitrogen, cooled to −10° C., was added dropwise sodium bis(trimethylsilyl)amide (1M in tetrahydrofuran, 5 mL). The mixture was allowed to warm to room temperature, and after 15 minutes ethyl iodide (0.30 mL) was added. After 15 minutes, methanol (1 mL) and ethyl acetate were added. The mixture was washed, dried (Na$_2$SO$_4$), filtered, and evaporated. Chromatography of the residue over silica gel (ethyl acetate/hexane) gave 5,11-dihydro-11-diethyl-5-methyl-10-oxodipyrid[3,2-b:2',3'-e]azepine-6-one (0.098 g).

Example 6

5,11-Dihydro-11-spirocyclopentyl-5-methyldipyrido[3,2-b:2',3'-e]azepine-6-one

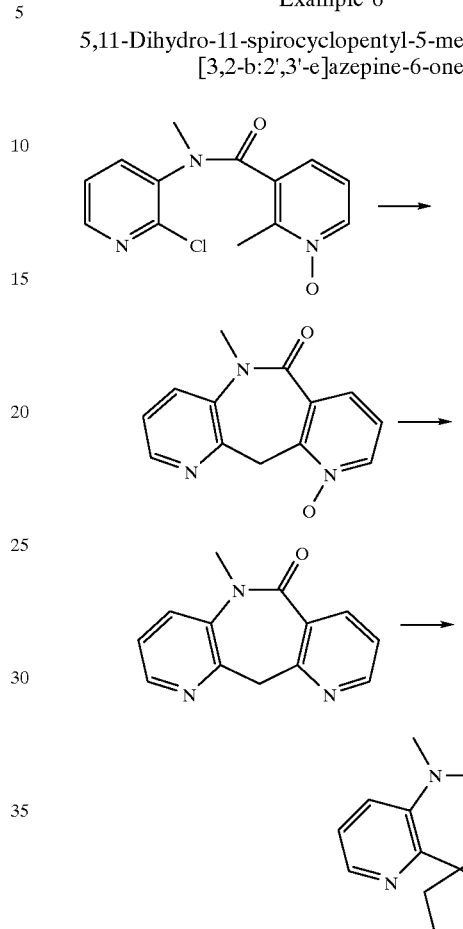

5,11-dihydro-5-methyl-10-oxodipyrid[3,2-b:2',3'-e]azepine-6-one

To a stirred solution of N-(2-chloro-3-pyridinyl)-N-methyl-2-methylnicotinamide N-oxide (1.02 g) in tetrahydrofuran (20 mL) under argon at room temperature, was added dropwise potassium tert-butoxide (1M in tetrahydrofuran, 7 mL). After 30 minutes, water was added, the mixture was diluted with methylene chloride, and the organic phase was separated, washed, dried (Na$_2$SO$_4$), filtered, and evaporated. Trituration of the residue gave 5,11-dihydro-5-methyl-10-oxodipyrid[3,2-b:2',3'-e]azepine-6-one (0.76 g) which was used directly in the next step.

5,11-dihydro-5-methyl-10-dipyrid[3,2-b:2',3'-e]azepine-6-one

To a solution of 5,11-dihydro-5-methyl-10-oxodipyrido[3,2-b:2',3'-e]azepine-6-one (0.199 g) in chloroform (3 mL) was added Lawessons reagent (0.140 g). The mixture was stirred for 30 minutes. Chromatography of the reaction mixture directly over silica gel (ethyl acetate/ethanol) gave 5,11-dihydro-5-methyldipyrido[3,2-b:2',3'-e]azepine-6-one (0.172 g).

5,11-Dihydro-11-spirocyclopentyl-5-methyldipyrido[3,2-b:2',3'-e]azepine-6-one.

To a solution of 5,11-dihydro-5-methyldipyrido[3,2-b:2',3'-e]azepine-6-one (0.069 g) in DMSO (0.6 mL) stirred at room temperature, was added potassium tert-butoxide (1M in tetrahydrofuran, 0.4 mL). After 2 minutes 1,4-diiodobutane (0.11 g) in DMSO (0.3 mL) was added. After 10 minutes, additional potassium tert-butoxide (0.4 mL) was added, and the mixture was stirred for 1 hour. The mixture was diluted with ethyl acetate, washed with water, dried, filtered, and evaporated. Fractionation of the residue by preparative layer chromatography gave 5,11-Dihydro-11-spirocyclopentyl-5-methyldipyrido[3,2-b:2',3'-e]azepine-6-one (0.019 g).

Example 7

5,11-Dihydro-11-ethyl-2-methoxy-5-methyl-10-oxodipyrido[3,2-b:2',3'-e]azepine-6-one

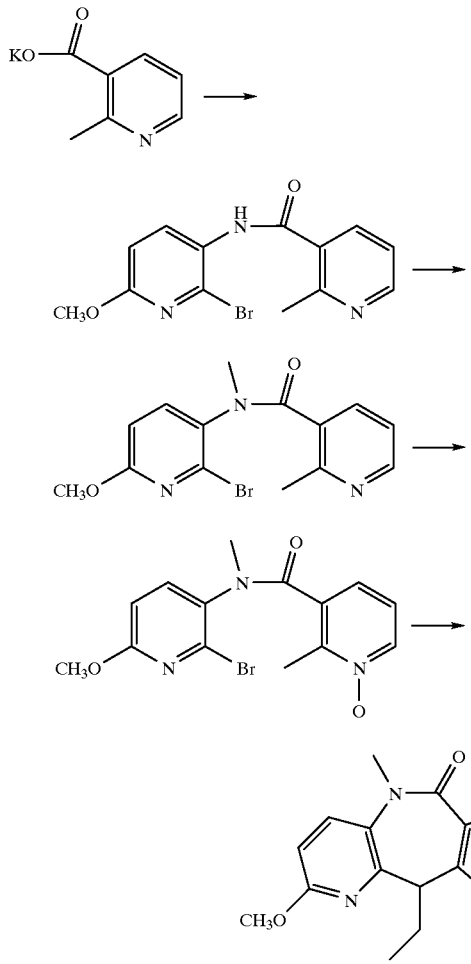

N-(2-Bromo-6-methoxy-3-pyridinyl)-2-methylnicotinamide

To a suspension of potassium 2-methylnicotinate (1.96 g) in chloroform (30 mL) was added thionyl chloride (2.5 mL). The mixture was stirred overnight at room temperature under a drying tube. Diisopropylethylamine (5 mL) was added followed by 3-amino-2-bromo-6-methoxypyridine (2.25 g). After 10 minutes additional diisopropylethylamine (5 mL) was added. After 2 hours the mixture was diluted with chloroform, washed with water, dried ($Na_2SO_4$,) filtered, and evaporated. Chromatography of the residue over silica gel (chloroform/methanol) gave N-(2-bromo-6-methoxy-3-pyridinyl)-2-methylnicotinamide (2.80 g).

N-(2-Bromo-6-methoxy-3-pyridinyl)-N-methyl-2-methylnicotinamide N-oxide

To a stirred solution of N-(2-bromo-6-methoxy-3-pyridinyl)-2-methylnicotinamide (1.61 g) in DMSO (5 mL) was added sodium bis(trimethylsilyl)amide (1M in tetrahydrofuran, 5.5 mL) followed by methyl iodide (0.25 mL). After 15 minutes, the mixture was diluted with ethyl acetate, washed with water, dried ($Na_2SO_4$), filtered, and evaporated. The residue was dissolved in acetic acid (5 mL) and 32% peracetic acid (5 mL), and was heated at 100° C. for 1 hour. The solvents were evaporated under reduced pressure. The residue was taken up in chloroform and washed with 5% aqueous sodium hydroxide. The organic phase was dried, filtered, and evaporated to give N-(2-bromo-6-methoxy-3-pyridinyl)-N-methyl-2-methylnicotinamide N-oxide which crystallized from ethyl acetate, (1.51 g).

5,11-dihydro-11-ethyl-2-methoxy-5-methyl-10-oxodipyrid[3,2-b:2',3'-e]azepine-6-one To a stirred solution of N-(2-bromo-6-methoxy-3-pyridinyl)-N-methyl-2-methylnicotinamide N-oxide (0.655 g) in tetrahydrofuran (15 mL) under argon was added dropwise potassium tert-butoxide (1M in tetrahydrofuran, 4 mL). The mixture was stirred at room temperature for 45 minutes, and ethyl iodide (0.2 mL) was added. After 1 hour, the mixture was diluted with chloroform, washed with water, dried ($Na_2SO_4$), filtered, and evaporated. Chromatography of the residue over silica gel (methylene chloride/ethanol) 5,11-dihydro-11-ethyl-2-methoxy-5-methyl-10-oxodipyrid[3,2-b:2',3'-e]azepine-6-one which crystallized on trituration with ether (0.416 g).

Example 8

5,11-Dihydro-11-ethyl-2-methoxy-5-methyl-dipyrido[3,2-b:2',3'-e]azepine-6-one

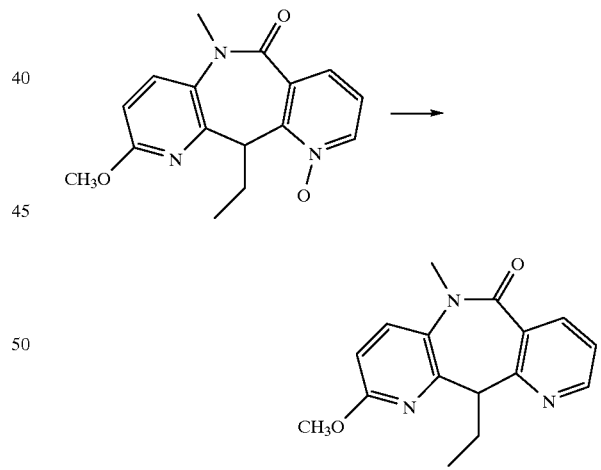

5,11-dihydro-11-ethyl-2-methoxy-5-methyl-10-oxodipyrid[3,2-b:2',3'-e]azepine-6-one.

A mixture of 5,11-dihydro-11-ethyl-2-methoxy-5-methyl-10-oxodipyrid[3,2-b:2',3'-e]azepine-6-one (0.041 g), and Lawessons reagent (0.030 g) in xylene (1 mL) was heated at 100 ° C. in a sealed tube for 2 hours. The mixture was fractionated directly by preparative layer chromatography (developer ethyl acetate/hexane 1/1) to give 5,11-dihydro-11-ethyl-2-methoxy-5-methyl-10-dipyrid[3,2-b:2',3'-e]azepine-6-one (0.022 g).

Example 9

5,11-Dihydro-11-diethyl-2-methoxy-5-methyl-dipyrido[3,2-b:2',3'-e]azepine-6-one

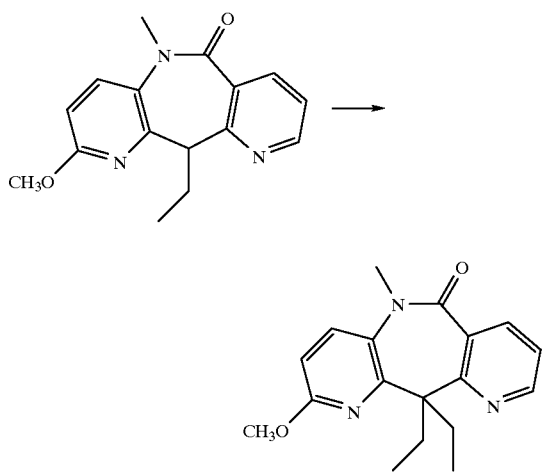

5,11-Dihydro-11-diethyl-2-methoxy-5-methyl-dipyrido[3,2-b:2',3'-e]azepine-6-one

To a stirred solution of 5,11-dihydro-11-ethyl-2-methoxy-5-methyl-10-dipyrid[3,2-b:2',3'-e]azepine-6-one (0.032 g) in DMSO (1 mL) was added potassium tert-butoxide (1M in tetrahydrofuran, 0.3 mL). After 5 minutes, ethyl iodide (0.1 mL) was added. After 20 minutes, the mixture was diluted with ethyl acetate, washed with water, dried, filtered, and evaporated. Fractionation of the residue by preparative layer chromatography (developer, ethyl acetate/hexane) gave 5,11-dihydro-11-diethyl-2-methoxy-5-methyl-dipyrido[3,2-b:2',3'-e]azepine-6-one (0.024 g).

Example 10

5,11-Dihydro-11-methylthio-2-methoxy-5-methyl-10-oxodipyrido[3,2-b:2',3'-e]azepine-6-one

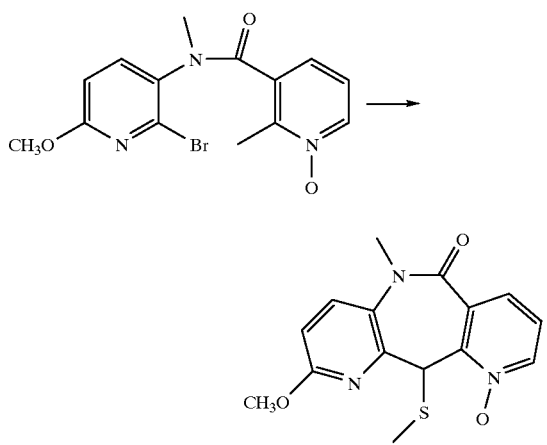

To a stirred solution of N-(2-bromo-6-methoxy-3-pyridinyl)-N-methyl-2-methylnicotinamide N-oxide (0.709 g) in tetrahydrofuran (15 mL) was added sodium bis(trimethylsilyl)amide (1M in tetrahydrofuran, 6 mL). After 2 hours, dimethyldisulfide (0.4 mL) was added and the mixture was stirred at room temperature overnight. The mixture was diluted with chloroform, washed with water, dried, filtered, and evaporated. Chromatography of the residue over silica gel (chloroform/ethanol) gave 5,11-dihydro-11-methylthio-2-methoxy-5-methyl-10-oxodipyrido[3,2-b:2',3'-e]azepine-6-one (0.183 g).

Example 11

5,11-Dihydro-11-methylthio-2-methoxy-5-methyl-dipyrido[3,2-b:2',3'-e]azepine-6-one

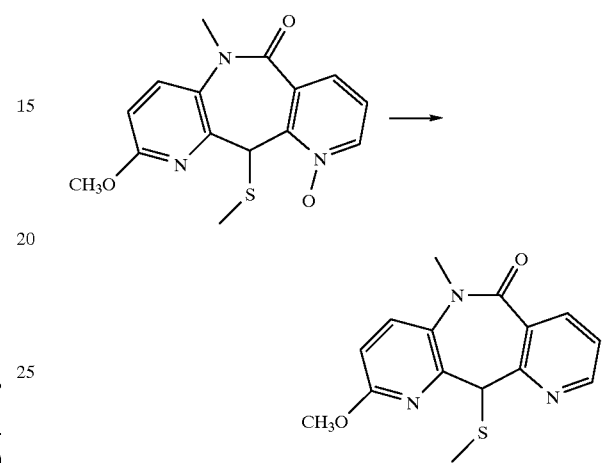

A mixture of 5,11-dihydro-11-methylthio-2-methoxy-5-methyl-10-oxodipyrido[3,2-b:2',3'-e]azepine-6-one (0.067 g) and Lawessons reagent (0.044 g) in xylene (3 mL) was stirred and heated at 90° C. for 20 minutes. The mixture was fractionated directly by preparative layer chromatography (developer, ethyl acetate/hexane) to give 5,11-dihydro-11-methylthio-2-methoxy-5-methyl-dipyrido[3,2-b:2',3'-e]azepine-6-one (0.061 g).

Example 12

5,11-Dihydro-11-methyl-11-methylthio-2-methoxy-5-methyl-dipyrido[3,2-b:2',3'-e]azepine-6-one

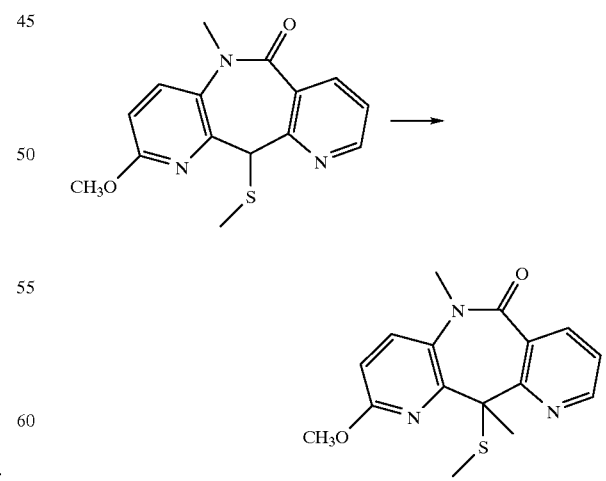

To a solution of 5,11-dihydro-11-methylthio-2-methoxy-5-methyl-dipyrido[3,2-b:2',3'-e]azepine-6-one (0.031 g) in DMSO (0.5 mL) stirred under argon was added potassium tert-butoxide (1M in tetrahydrofuran, 0.012 mL). After 1 minute, methyl iodide (0.05 mL) was added. After 5 minutes the mixture was diluted with ethyl acetate, washed with water, dried, filtered and evaporated. Fractionation of the residue by preparative layer chromatography (developer, ethyl acetate/hexane) gave 5,11-dihydro-11-methyl-11-methylthio-2-methoxy-5-methyl-dipyrido[3,2-b:2',3'-e]azepine-6-one (0.029).

Example 13

5,11-Dihydro-11-ethyl-2-(4-pyrazolyl)-5-methyl-dipyrido[3,2-b:2',3'-e]azepine-6-one

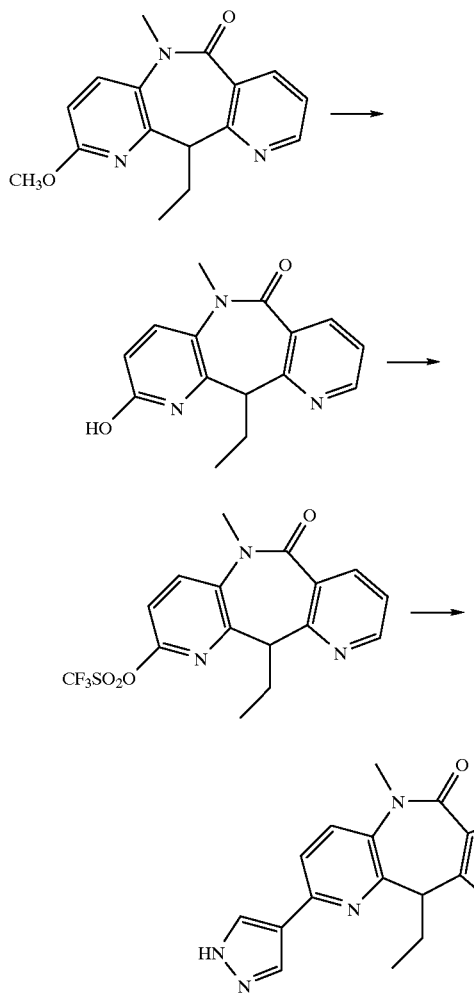

5,11-Dihydro-11-ethyl-2-trifluoromethanesulfonyloxy-5-methyl-dipyrido[3,2-b:2',3'-e]azepine-6-one A solution of 5,11-dihydro-11-ethyl-2-methoxy-5-methyl-dipyrido[3,2-b:2',3'-e]azepine-6-one (0.181 g) in acetic acid (1 mL) and 48% HBr in acetic acid (1 mL) was heated at 110° C. for 10 minutes. The mixture was cooled, neutralized with saturated sodium bicarbonate, and extracted with chloroform. The organic phase was dried, filtered and evaporated to give 5,11-dihydro-11-ethyl-2-hydroxy-5-methyl-dipyrido[3,2-b:2',3'-e]azepine-6-one (0.176 g) which was used directly in the next reaction.

To a solution of 5,11-dihydro-11-ethyl-2-hydroxy-5-methyl-dipyrido[3,2-b:2',3'-e]azepine-6-one (0.176 g) in chloroform (10 mL) cooled on ice was added triethylamine (0.25 mL) followed by triflic anhydride (0.2 mL). After 10 minutes, the mixture was diluted with ethyl acetate, washed with water, dried, filtered, and evaporated. Chromatography of the residue over silica gel (ethyl acetate/hexane) gave 5,11-dihydro-11-ethyl-2-trifluoromethanesulfonyloxy-5-methyl-dipyrido[3,2-b:2',3'-e]azepine-6-one (0.165 g).

5,11-Dihydro-11-ethyl-2-(4-pyrazolyl)-5-methyl-dipyrido[3,2-b:2',3'-e]azepine-6-one A mixture of 5,11-dihydro-11-ethyl-2-trifluoromethanesulfonyloxy-5-methyl-dipyrido[3,2-b:2',3'-e]azepine-6-one (0.084 g), 4-tributylstannylpyrazole (0.096 g), lithium chloride (0.052 g) and Pd(Ph$_3$P)$_2$Cl$_2$ (0.009 g) in dimethylformamide (1 mL) was heated at 120° C. in a sealed tube 16 hours. The mixture was diluted with ethyl acetate, washed with water, dried, filtered and evaporated. Chromatography of the residue over silica gel (ethyl acetate/hexane) gave 5,11-dihydro-11-ethyl-2-(4-pyrazolyl)-5-methyl-dipyrido[3,2-b:2',3'-e]azepine-6-one (0.010 g).

Example A

Capsules or Tablets

| | A-1 | | A-2 | |
|---|---|---|---|---|
| Ingredients | Quantity | Ingredients | | Quantity |
| Compound of Ex. 12 | 250 mg | Compound of Ex. 12 | | 50 mg |
| Starch | 160 mg | Dicalcium Phosphate | | 160 mg |
| Microcrys. Cellulose | 90 mg | Microcrys. Cellulose | | 90 mg |
| Na Starch Glycolate | 10 mg | Stearic acid | | 5 mg |
| Magnesium Stearate | 2 mg | Sodium Starch Glycolate | | 10 mg |
| Fumed colloidal silica | 1 mg | Fumed colloidal silica | | 1 mg |

The compound of Example 13 is blended into a powder mixture with the premixed excipient materials as identified above with the exception of the lubricant. The lubricant is then blended in and the resulting blend compressed into tablets or filled into hard gelatin capsules.

Example B

Parenteral Solutions

| Ingredients | Quantity |
|---|---|
| Compound of Example 12 | 500 mg |
| Tartaric acid | 1.5 g |
| Benzyl Alcohol | 0.1% by weight |
| Water for injection | q.s. to 100 mL |

The excipient materials are mixed with the water and thereafter the compound of Example 13 is added. Mixing is continued until the solution is clear. The pH of this solution is adjusted to 3.0 and is then filtered into the appropriate vials or ampoules and sterilized by autoclaving.

Example C

Nasal Solutions

| Ingredients | Quantity |
|---|---|
| Compound of Example 12 | 100 mg |
| Citric acid | 1.92 g |

-continued

| Ingredients | Quantity |
|---|---|
| Benzalkonium chloride | 0.025% by weight |
| EDTA | 0.1% by weight |
| Polyvinylalcohol | 10% by weight |
| Water | q.s to 100 mL |

The excipient materials are mixed with the water and thereafter the compound of Example 13 is added and mixing is continued until the solution is clear. The pH of this solution is adjusted to 4.0 and is then filtered into the appropriate vials or ampoules.

What is claimed is:

1. A compound of the formula 1

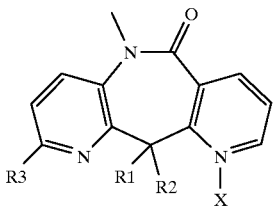

1 wherein:

X is an oxygen atom or nothing;

R$^1$ is hydrogen, alkyl of 1 to 4 carbon atoms, fluoroalkyl of 1 to 4 carbon atoms and 1 to 3 fluorine atoms, cycloalkyl of 3 to 6 carbon atoms, alkylthio of 1 to 2 carbon atoms, alkyloxy of 1 to 2 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 4 carbon atoms, alkyloxyalkyl or alkylthioalkyl of 2 to 3 carbon atoms, alkanoyl or alkyl(thiocarbonyl) of 2 to 5 carbon atoms, or cyanoalkyl of 2 to 3 carbon atoms;

R$^2$ is hydrogen, methyl or ethyl;

R$^3$ is a hydrogen atom, alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxy or alkylthio of 2 to 6 carbon atoms, alkyloxyalkyl or alkylthioalkyl of 2 to 6 carbon atoms, pyrrolidinyl, pyrrolinyl, piperidinyl, mono- or di-alkylamino wherein each alkyl moiety contains 1 to 3 carbon atoms, halogen, cyano, nitro, or carboxyl, aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by hydroxyl, amino, halogen, alkyl or alkyloxy of 1 to 3 carbon atoms.

2. A compound of formula 1, as set forth in claim 1, wherein:

X is nothing;

R$^1$ is hydrogen, alkyl of 1 to 3 carbon atoms, cycloalkyl of 3 to 4 carbon atoms, alkylthio of 1 to 2 carbon atoms;

R$^2$ is hydrogen, methyl or ethyl;

R$^3$ is a hydrogen atom, methyl, trihalomethyl, alkyloxy or alkylthio of 1 to 2 carbon atoms, pyrrolidinyl, pyrrolinyl, piperidinyl, di-alkylamino wherein each alkyl moiety contains 1 to 2 carbon atoms, halogen, cyano, aryl (wherein aryl is phenyl, pyridinyl, thienyl, furanyl, pyrrolyl, imidazolyl, pyrazolyl, oxazoly), isoxazolyl, thiazolyl or isothiazolyl) which is either unsubstituted or substituted by hydroxyl, amino, halogen, alkyl or alkyloxy of 1 to 3 carbon atoms.

3. 5,11 dihydro-11-ethyl-2-methoxy5-methyl-dipyrido[3,2-b:2',3'-e]azepine-6-one;

5,11-dihydro-11-ethyl-2-(4-pyrazolyl)-5-methyl-dipyrido[3,2-b:2',3'-e]azepine-6-one, and the pharmaceutically acceptable salts thereof.

4. A method for inhibiting HIV-1 replication in a human host infected by HIV-1, which comprises administering to such host an amount of a compound of formula 1, as set forth in claims 1, 2, or 3, or a pharmaceutically acceptable salt thereof, which is sufficient to inhibit HIV-1 replication.

5. A method for treating HIV-1 infection which comprises administering, to a human being exposed to or infected by HIV-1, a therapeutically effective amount of a compound of formula 1, as set forth in claims 1, 2, or 3, or a pharmaceutically acceptable salt thereof.

6. A pharmaceutical composition suitable for treating HIV-1 infection which comprises a therapeutically effective amount of a compound of formula 1, as set forth in claims 1, 2, or 3, or a pharmaceutically acceptable salt thereof, and a pharmaceutically acceptable carrier.

* * * * *